(12) United States Patent
Ruimi et al.

(10) Patent No.: US 8,077,826 B2
(45) Date of Patent: Dec. 13, 2011

(54) CT SCANNER WITH SCATTER RADIATION CORRECTION AND METHOD OF USING SAME

(75) Inventors: David Ruimi, Ganot Hadar (IL); Olga Shapiro, Haifa (IL); Ehud Dafni, Caesarea (IL)

(73) Assignee: Arineta Ltd., Caesarea (IL)

( * ) Notice: Subject to any disclaimer, the term of this patent is extended or adjusted under 35 U.S.C. 154(b) by 184 days.

(21) Appl. No.: 12/480,079

(22) Filed: Jun. 8, 2009

(65) Prior Publication Data

US 2009/0304142 A1    Dec. 10, 2009

Related U.S. Application Data

(60) Provisional application No. 61/131,302, filed on Jun. 9, 2008.

(51) Int. Cl.
*G01N 23/00* (2006.01)

(52) U.S. Cl. .............................................. 378/7; 378/19

(58) Field of Classification Search .................. 378/4, 6, 378/7, 9, 15, 19, 901
See application file for complete search history.

(56) References Cited

U.S. PATENT DOCUMENTS

2011/0064190 A1 *   3/2011   Ruimi et al. .................... 378/44
* cited by examiner

*Primary Examiner* — Jurie Yun
(74) *Attorney, Agent, or Firm* — William H. Dippert; Eckert Seamans Cherin & Mellott, LLC

(57) ABSTRACT

A CT scanner with scatter correction device and a method for scatter correction are provided. The method of correcting CT images from artifacts caused by scattered radiation comprises affixing to the non-rotating frame of the CT gantry a plurality of shields for shielding some of the CT detector elements from direct X ray radiation, while allowing scattered radiation to arrive at said shielded elements; measuring scatter signals from said shielded elements, indicative of scattered radiation intensity; and correcting for scatter by subtracting scatter intensity values estimated from said measured scatter signals from signals measured by unshielded detector elements.

29 Claims, 11 Drawing Sheets

CT SCANNER WITH SCATTER RADIATION CORRECTION AND METHOD OF USING SAME

CROSS-REFERENCE TO RELATED APPLICATION

This application is based upon and claims the benefit of U.S. Provisional Application Ser. No. 61/131,302, filed Jun. 9, 2008 and entitled "CT scanner with scatter radiation correction and method of using the same", the entire contents of which are incorporated by reference as if fully set forth herein.

FIELD OF THE INVENTION

The present invention relates to Computed Tomography (CT) imaging. More specifically, it relates to measurement and compensation of scattered radiation in wide beam CT scanners.

BACKGROUND OF THE INVENTION

Computed Tomography (CT) is a common imaging technique based on measurements of X-ray attenuation in the scanned subject in multiplicity of projection angles. X-rays are attenuated by either absorption or scattering, in which case they may still reach the detector and be detected. Scatter radiation reduction and correction are required for both medical and nonmedical X ray CT imaging applications. Due to scattered X-ray photons, the local contrast and the data accuracy are deteriorated. Various methods to reduce and compensate for the scattering effect have been suggested and had being used. Early CT scanners have used narrow fan beams and were assisted by antiscatter grids so scatter radiation was not a major obstacle in these systems. However, in modern CT scanners, large area X-ray detectors having a plurality of detector element arranged in rows and columns are used to perform multi-slice imaging. In these multi-slice systems the width of the beam is significantly larger than in earlier single slice CT. Accordingly; the adverse effect of scattering is intensified. Further, some CT scanners use multiple sources of X rays associated with multiple detectors and the cross scattering increases the scattering problem.

In U.S. Pat. No. 5,666,391 to B. Ohnesorge, et al. (Sep. 9, 1997) the inventors suggest to correct for the scattered radiation by calculating a theoretical scattering distribution, based on the subject contour and shape as reconstructed from the data before the correction is applied, and subtracting the calculated scattering data from the actual collected data. The accuracy of this correction method is rather limited due to the high variability of scanned subjects.

In U.S. Pat. No. 6,618,466 to N. Ruola (Sep. 9, 2003), the inventor suggests positioning an array of shields between the radiation source and the scanned subject, acquiring some views of the subject from some angels wherein the shielded areas of the detector are used to measure the scattered radiation, removing the shields array and scanning the subject without the array. The scattering data collected in the first scan for certain parts of the detector and certain view angles are used to calculate the scattering map by interpolation for the entire array and for all view angles and then to correct the data of the second scan.

In U.S. Pat. No. 7,336,759 to N. Masatak (Feb. 26, 2008), the inventor suggests collecting in addition to the "main scan" to be corrected, which is done with a wide beam, additional few views with narrow beam. The data with narrow beam is used to assess the effect of the scattered radiation at the same projections, and to interpolate the scattering distribution from these measurements to the wide beam.

However, none of these methods provides a solution for accurate measurement and compensation for the scattered radiation without adding steps to the clinical procedure and without exposing the subject to additional radiation.

U.S. provisional patent application filed on 8 of May 2008 entitled "X RAY IMAGING SYSTEM WITH SCATTER RADIATION CORRECTION AND METHOD OF USING SAME" by the authors of the present invention, now submitted as PCT Application No. PCT/IL2009/000470, discloses an imaging system wherein radiation shield positioned in front of certain parts of the detector during subject scanning yield data which is useful to assess the scattered radiation and correct for it. In a CT scanner according to the said disclosure certain detector elements are shielded from radiation at all projection angles and do not contribute directly to the images, which might be undesirable.

SUMMARY OF THE INVENTION

The present invention relates to Computed Tomography (CT) imaging. More specifically, it relates to measurement and compensation of scattered radiation in wide beam CT scanners Accordingly, the object of the present invention is to provide an apparatus and a method of measuring the radiation scatter in the CT system during the imaging of a subject, and compensating for the scattered radiation effects.

A feature of the invention is the measurement of scattered radiation through use of radiation opaque shields placed in the imaging system during the acquisition whereby substantially only scattered radiation is received by the shielded areas of the detector at certain projection angles. The scattered radiation for the entire detectors matrix at all rotation angles can then be interpolated from the measured scattered radiation in the shielded detector elements; and then it can be subtracted from the measured data.

According to one aspect of the current invention, a method for CT imaging of a subject while correcting for scattered radiation is provided, the method comprising: providing a CT scanner comprising at least a first source of X ray radiation capable of rotating about the subject and a detector capable of receiving radiation that has been attenuated by said subject; providing array of radiation shields, said shields are operative to shield parts of the detector area from the X ray source at some source rotation angles and not to shield same parts of the detector area at other source rotation angles of said X ray source; irradiating said subject by said first X ray source while the source is rotating about said subject and acquiring X ray data from said detector, wherein X rays received by said detector comprise direct radiation from the source that was attenuated by said subject and scattered radiation that was scattered by said subject, and wherein parts of the detector area are substantially irresponsive to direct radiation and responsive to scattered radiation while they are shielded from said first X ray source by said shields; computing scattered radiation data indicative of the part of the X-ray data due to scattered radiation for all parts of the detector area at all rotation angles, said computation is based on data received by parts of the detector area while shaded by said shields; and correcting the data acquired by parts of the detector area not shielded by said shields by substantially subtracting said computed scattered radiation data from the total measured data.

In some embodiments, the method further comprising correcting data received by parts of the detector while shaded by the shields, wherein said correction is based on data received by parts of the detector while not shaded by said shields.

In some embodiments, the method further comprising reconstruction at least one image based on said corrected data.

In some embodiments said first X ray source and said detector are mounted on a rotating frame and said array of shields is mounted on a non rotating frame.

In some embodiments said detector is divided to detector elements and said shields comprise radiation opaque material substantially blocking direct radiation from reaching a part of the active area of shielded detector elements at certain source rotation angles.

In some embodiments said array of radiation shields is disposed on a cylinder made of radiation translucent material situated around said subject.

In some embodiments said array of shields comprises strips of radiation opaque material disposed on said cylinder.

In some embodiments said shields are positioned out of the beam path when said shields are proximate to said source and are positioned in the beam path when said shields are far from the source, as the source rotates about the subject.

In some embodiments said CT scanner further comprises a second X ray source displaced from said first X ray source.

In some embodiments said multiple sources are operable to irradiate a common detector area, wherein shields are configured to shield direct radiation from said first X ray source from reaching certain parts of the detector at certain rotation angles, said certain parts capable to receive direct radiation from said second X ray source at the same rotation angle.

In some embodiments said process of the scatter correction comprises a fit of a scatter map for the detector area, based on the readout of said shielded detector elements.

In some embodiments said fit comprises using a polynomial function.

In some embodiments said process of the scatter correction comprises performing spatial interpolation on read out of shielded detector elements.

In some embodiments said spatial interpolation comprises cubic or higher order spline interpolation.

In some embodiments said shields are movable out of the beam path or to a different position in the beam path.

According to another aspect of the current invention, a system for CT imaging of a subject while correcting for scattered radiation is provided, the system comprising: at least a first source of X ray radiation capable of rotating about the subject; a detector capable of receiving radiation that has been attenuated by said subject; an array of radiation shields, said shields are operative to shield parts of said detector area from said first X ray source at some source rotation angles and not to shade same parts of the detector area at other source rotation angles; a controller capable of irradiating said subject by the X ray source while the source is rotating about the subject and acquiring X ray data from said detector, wherein X rays received by said detector comprise direct radiation from the source that was attenuated by the subject and scattered radiation that was scattered by the subject, and wherein parts of the detector area are substantially irresponsive to direct radiation and responsive to scattered radiation while they are shielded from the X ray source by said shields; an image processor capable of computing the part of the X-ray data due to scattered radiation for all parts of the detector area at all rotation angles, said computation is based on data received by parts of said detector area while shielded by said shields; an image processor capable of correcting the data received by parts of the detector area not shielded by the shields by subtraction of the computed scattered radiation data from the total measured data.

In some embodiments said system further comprising an image processor capable of correcting the data received by parts of the detector shielded by said shields, wherein said correction is based on data received by parts of the detector not shielded by said shields.

In some embodiments said system further comprising an image processor capable of reconstructing images of said subject.

In some embodiments said X ray source and said detector are mounted on a rotating frame and the array of shields is mounted on a non rotating frame.

In some embodiments said detector is divided to detector elements and said shields comprises radiation opaque material that block substantially all direct radiation from reaching shielded detector elements at certain source rotation angles.

In some embodiments said system further comprising a cylinder made of radiation translucent material situated around said subject and said shields comprise of elements of radiation opaque material disposed on said cylinder.

In some embodiments said shields comprise strips of radiation opaque material disposed on said cylinder.

In some embodiments said shields are positioned out of the beam path when said shield are proximate to said first X ray source and are positioned in the beam path when said shield are far from said X ray source, as the source rotates about the subject.

In some embodiments said system further comprising at least a second X ray sources displaced from said first X ray source.

In some embodiments said multiple sources are operable to irradiate a common detector area, wherein said shields are operable to shield direct radiation from said first X ray source from reaching certain parts of the detector at certain rotation angles, said certain parts capable to receive direct radiation from said second X ray source at the same rotation angle.

In some embodiments said process of the scatter correction comprises a fit of a scatter map for said detector area, based on the readout of shielded detector elements.

In some embodiments said fit comprises using a polynomial function.

In some embodiments said process of the scatter correction comprises performing spatial interpolation on readout of shielded detector elements.

In some embodiments said spatial interpolation comprises cubic or higher order spline interpolation.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DETAILED DESCRIPTION OF THE INVENTION

Figure 1A:
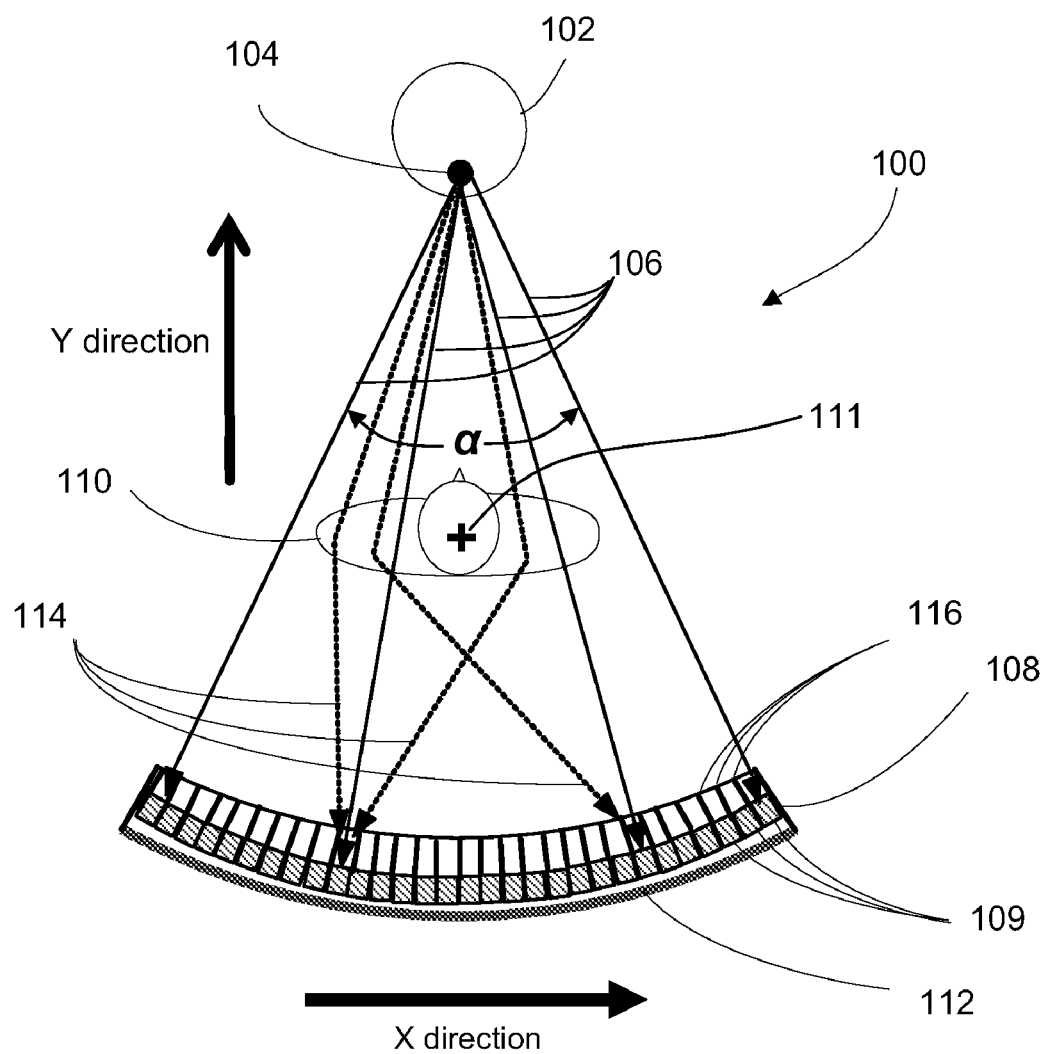
FIG. 1a schematically depicts a front view of a prior art CT scanner.

The present invention relates to Computed Tomography (CT) imaging. More specifically, it relates to measurement and compensation of scattered radiation in wide beam CT scanners Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

In discussion of the various figures described herein below, like numbers refer to like parts.

The drawings are generally not to scale. For clarity, non-essential elements were omitted from some of the drawings.

Figure 1B:
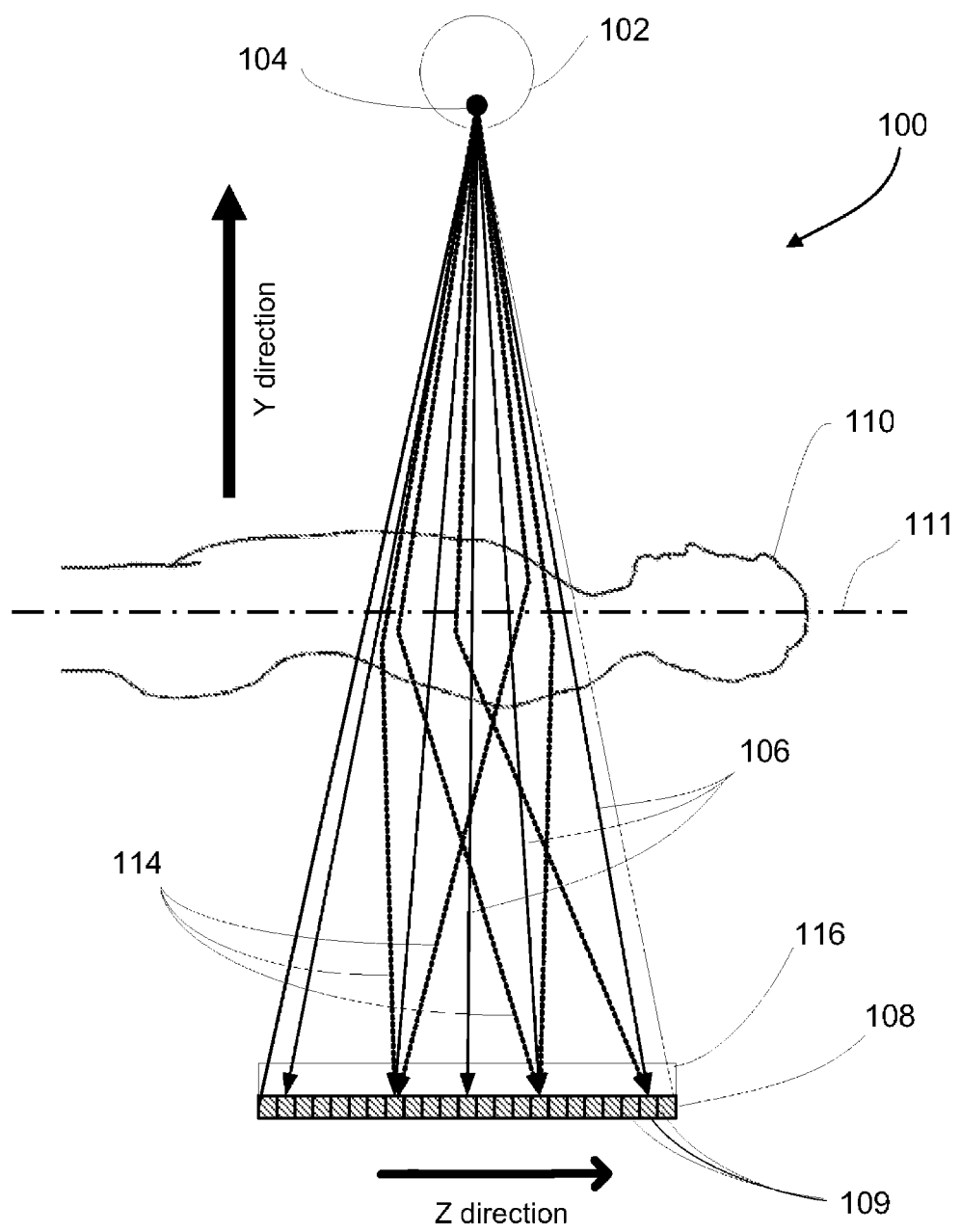
FIG. 1b schematically depicts a side view of a prior art CT scanner.

FIG. 1a schematically depicts a front view of a prior art CT scanner; while FIG. 1b schematically depicts a side view of a prior art CT scanner.

FIG. 1a (front view) and 1b (side view) show a prior art cone beam CT scanner 100. X ray source 102 with focal spot 104 emits a beam of X radiation 106 collimated to illuminate detector array 108. Typically the source-detector pair is mounted on a rotating section of the CT gantry (not seen in these figures for clarity), rotating about an axis of rotation 111. The subject to be examined 110 is positioned between the source and the detector. Detector array 108 may be composed of discrete elements arranged in rows and columns, a flat panel detector or other type of X-ray detector. It may have a spherical or arc shape centered about the focal spot (as shown), be planar or have other surface curvature. Herein below we refer to "columns" of the detector as the detector elements arranged in the direction parallel to the rotation axis (Z direction) and "rows" of the detector as the detector elements arranged in the direction of the detector perpendicular to the rotation axis (X direction).

Attenuation data for X rays 106 that have been emitted during scan, attenuated by subject 110 and received by detector elements 109 of detector array 108 are acquired by dedicated electronic circuits 112. This data is transmitted to an image processor (not shown in these figures for clarity) and used for calculating the Attenuation Coefficient of their path 106 through the subject 110, and then, reconstructed to images by algorithms known in the art; for example Filtered Back Projection (FBP) or iterative algorithms. Reconstructed images are displayed and stored for further processing. CT scanning can be done in single acquisitions during rotation of the source and detector by at least 360° (referred to as full scan) or at least 180°+α (wherein α is the angular span of the cone beam about the center of rotation 111, referred to as partial scan). Scanning can be done also with continuous rotation combined with subject translation (referred to as spiral or helical scan).

In the description of embodiments of the invention the following coordinate system is used: Z is parallel to the rotation axis, Y is pointing from the rotation axis to the X ray source and X is tangent to the focal spot trajectory. The coordinate system is rotating with the rotor gantry frame.

Various parts of the CT scanner 100, including the gantry, subject support, data acquisition system, controllers, image processors, display unit and other parts common to CT scanners are not shown in FIGS. 1a and 1b and subsequent figures for obviousness. A person skilled in the art will appreciate these parts are provided and included in the systems.

In FIGS. 1a and 1b, one may notice that some X-rays such as represented by numeral 114 that, as a result of the interaction with the subject 110, have been scattered, and impinged on detector elements that are not positioned in the direct path of the X ray as it was emitted from focal spot 104. The scattered radiation intensity detected by the detector increases the statistical noise, reduces the image contrast and results in various image artifacts. The distribution of the scattered photons is highly dependent on the scattering subject 110. Therefore, scatter reduction and correction are required to improve image accuracy for both medical (for example: human patient diagnostics, small animal imaging) and non-medical imaging applications (for example: explosive detection and nondestructive testing).

Much of the scattered radiation can be efficiently eliminated by using post patient collimator, usually referred to as antiscatter grid, which limits each detector cell's field of view to the vicinity of the x-ray focal spot. In prior art third generation fan beam CT scanners, the radiation beam is fan shaped. Antiscattering can be accomplished relatively easily by employing a one-dimensional array of collimator leafs 116 as marked in FIG. 1a and FIG. 1b. Leafs of array 116 are positioned near the surface of the detector and are focused at the x-ray focal spot 104.

One dimensional antiscatter 116 is efficient in rejecting radiation that was scattered azimuthally respective of the rotating gantry but it is not efficient in rejecting radiation scattered in a direction substantially along the detector columns (the columns defined being parallel to the rotation axis). Therefore, as demonstrated in FIG. 1b, in a wide beam CT (also called cone beam CT), with a one-dimensional antiscatter array, significantly more scattered radiation is detected by each detector element 109 than in a narrow beam CT. One solution to reduce scatter radiation level is to provide a two dimensional antiscatter grid near the surface of the detectors. This solution is mechanically complicated and expensive.

The aim of this invention is to suggest a method for measuring and correcting for the scattered radiation during a CT scan or other digital X ray imaging procedures involving rotation of the source.

Figure 2:
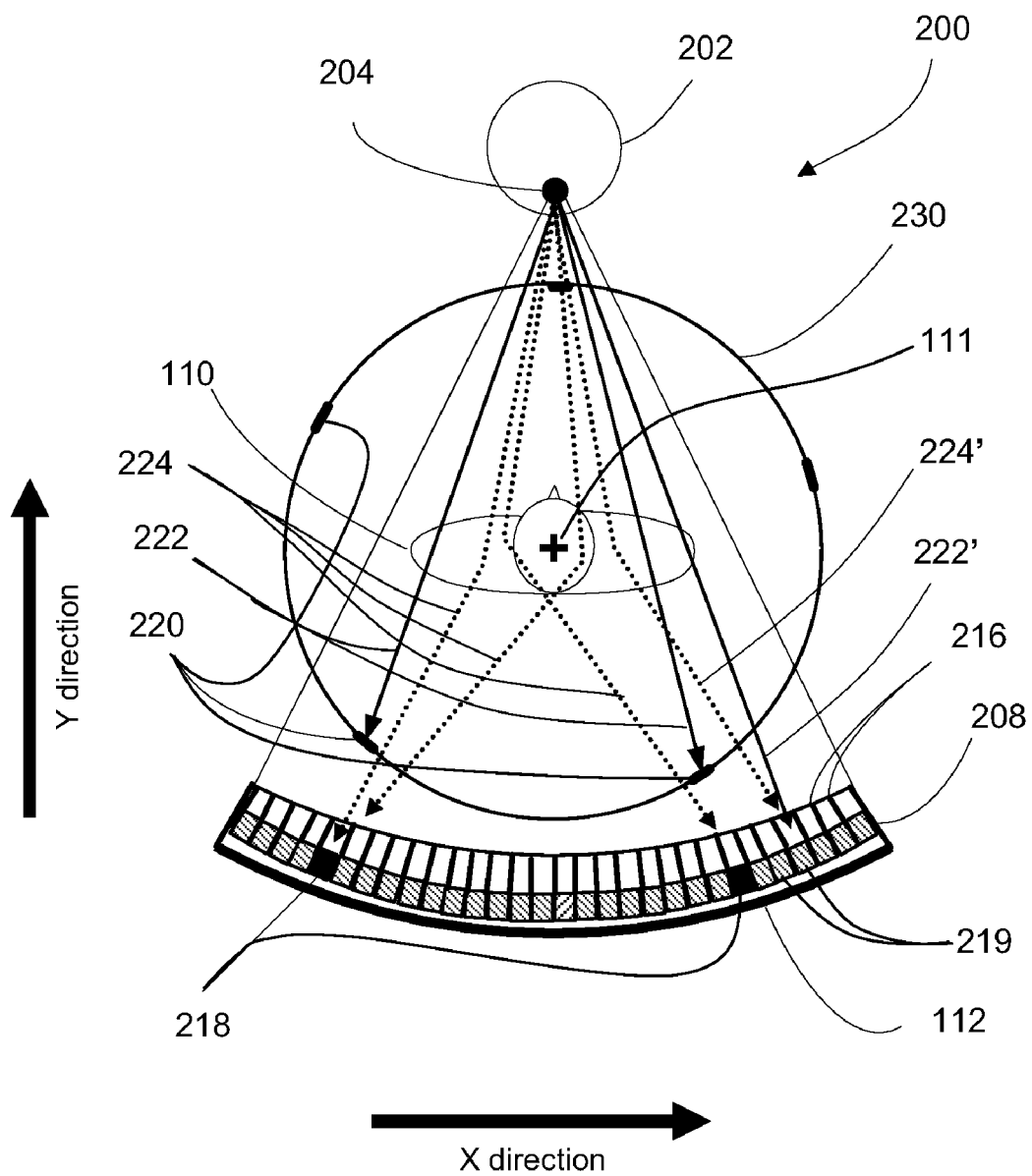
FIG. 2 schematically illustrates a front view of CT system according to an exemplary embodiment of the present invention.

FIG. 2 schematically illustrates a front view of a CT system 200 according to an exemplary embodiment of the present invention.

Detector 208 is shown to be divided to detector elements. In system 200, a cylinder 230 made of radiation translucent material such as 1 mm thick polycarbonate is provided as a part of the external covers of the CT gantry. Radiation opaque shields 220 are disposed on cylinder 230 and at a given gantry rotation angle are operative to block direct (un-scattered) X-ray 222 from being received by a particular sub-set of detector elements 218. On the other hand, most scattered radiation 224 is capable of impinging on shielded detector elements 218. If the detector 208 is irradiated without the presence of a scattering body such as scanned subject 110, the parts of the detector which are not shielded by shields 219 receive the direct radiation 222 from the source 202 whereas the parts of the detector which are shielded 218 receive substantially no radiation at all. As the source 202 and detector array 208 rotate about the patient 110 while shields 220 do not rotate, at any gantry angle different detectors elements are shielded by shields 220.

The external covers of the CT gantry (not seen in these figures for clarity) is substantially stationary and do not rotate with the rotor of the CT system. However, in some systems the CT gantry may tilt for performing oblique imaging. In these cases, the cover (and preferably the cylinder 230) may tilts with the rotor. The cover is typically used to protect the subject 110 from injury caused by rotating parts of the rotor such as X ray source 202, the detector, etc. Cylinder 230 may be part of the cover, or alternatively, it may be positioned inside the cover. Cylinder 230 may be made of materials other than polycarbonate, such as Mylar, etc. Optionally, thickness of cylinder 230 may be different than 1 mm. For example, cylinder 230 may be thin and flexible and gain its structural rigidity from being attached to the cover or to other supporting structure attached to the non-rotating part of the gantry. Optionally, cylinder 230 may comprise a strip or a plurality of strips to be glued to the cover. For retrofitting an existing CT system, the cover may be replaced with a cover having shields 220. Shields 220 may be attached to the cover, preferably to the surface away from the patient. Alternatively, shield 220 may be embedded in cylinder 230. In some embodiments, shields 220 may made of a free standing mash.

System 200 and other embodiments described hereinbelow have a controller operable to irradiate the patient, control motion of the gantry and acquire data from the detector. Further, they have an image processor operable to process the acquired data as described hereinbelow.

In embodiments of the present invention shields 220 are distributed over the circumference of cylinder 230. Preferably shields are disposed every 100 or every 200 or at other angular increments. In some preferred embodiments the shields 220 are composed of discrete elements made of heavy metal such as Lead, Tantalum, tungsten or tungsten alloy or of other material known in the art as efficient X ray absorber. Shields 220 may have a thickness of 1 mm or 2 mm or other value in the direction of the direct beam. Thickness of 1 mm respective the beam direction gives good results for shields made of Tungsten or Tantalum. Preferably, thickness of shield 220 is selected such that the attenuation of the shield to X ray emitted by source 202 is substantial. For example, causing the transmission of the direct beam 222 through shield 220 to be less than 1%. Optionally, higher attenuation is selected. Thickness of shield 220 may be selected depending on the material used for the shield and the X ray energy range used as attenuation depends on both. Optionally, attenuation of shield 220 is selected such that the direct radiation 222 which penetrate through the shield is comparable or preferably substantially smaller than the typical scattered radiation which may be scattered onto the shaded element 218 when a typical subject 110 is imaged.

Cylinder 230 may be positioned between 50 mm to 150 mm from the center of detector 208 surface although lower or higher distances are also possible. Optionally, the gap between shield 220 and the surface of detector 208 is determined according to system geometry and the size of detector elements 218. The gap between shield 220 and the surface of element 218 allows scattered beams 224 to reach the shielded element 218.

For scanner geometry wherein the detector 208 has an arc shape centered about the focal spot, as shown in FIG. 2, the distance from the shields 220 to shaded detector elements 218 in the wings of the arc is larger than the distance to shaded detector elements 218 in the center of the arc. Additionally, shields appear tilted differently in respect to the beam at different locations. Accordingly, different size of detector area may be shaded by a given shielding element 220 at the wings than in the center.

It should be noted that while direct radiation 222 is blocked by shield 220, and cannot arrive at detector element 218, scattered radiation 226 arrived at element 218 and detected. In contrast, unshielded detector element 219, in the neighborhood of shielded element 218 receives both direct radiation 222' and scattered radiation 224'. Scattered radiation is statistically similar in neighboring and close-by elements. Thus scattered radiation 224', detected together with direct radiation 222' on element 219, may be estimated from the radiation 224 detected by shielded element 218.

Figure 3A:
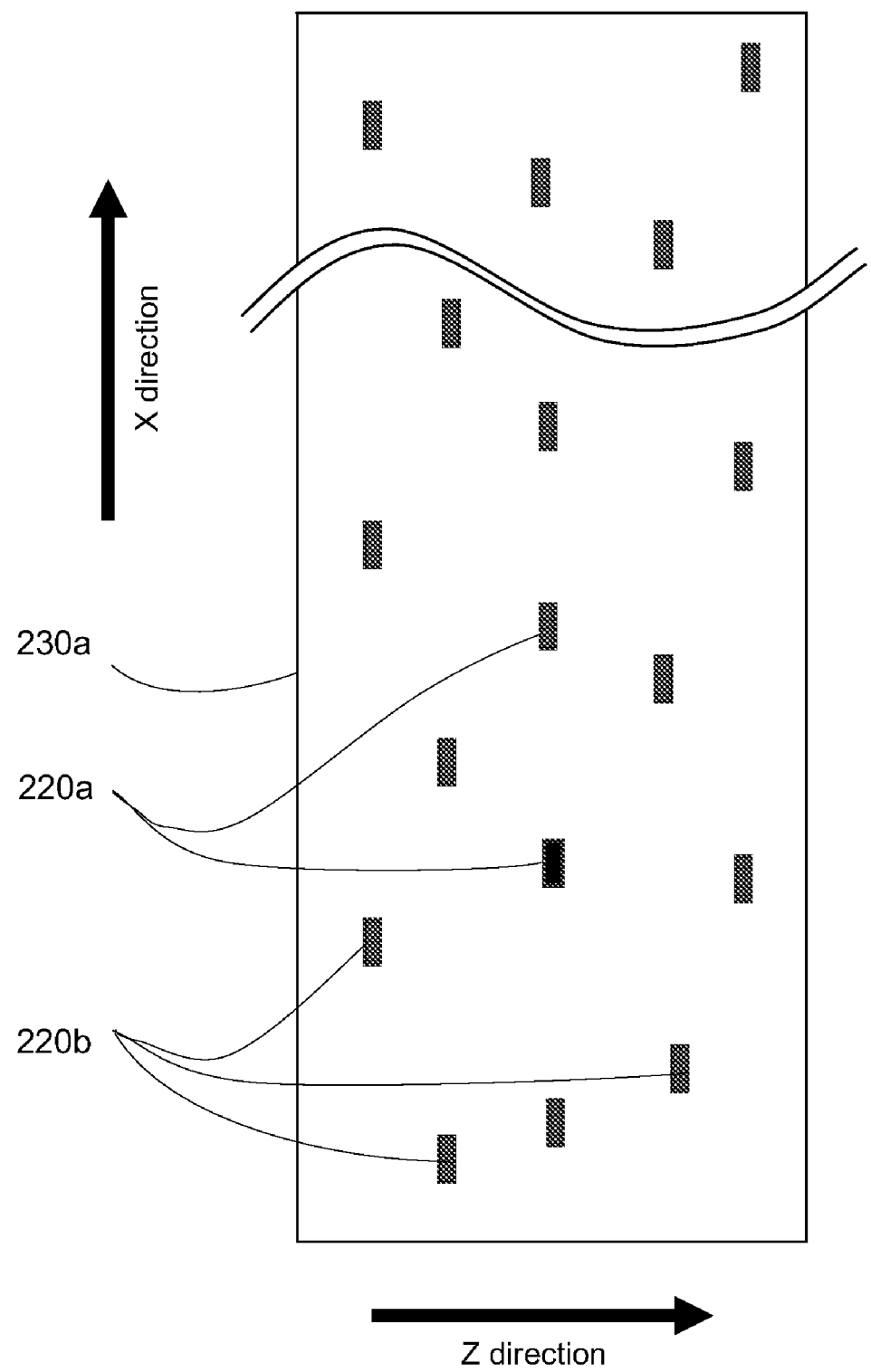
FIG. 3a schematically illustrates a section of the surface of cylinder having a plurality of shields according to an exemplary embodiment of the current invention.

FIG. 3a schematically illustrates a section of the surface of cylinder 230a according to an exemplary embodiment of the current invention (the cylinder surface is spread out for the illustration).

In the depicted exemplary embodiments, shields 220 are arranged in rows aligned with the X direction wherein row of shields 220a is central and substantially aligned with the center of the detector. Rows of shields 220b are positioned on both sides of row of shields 220a.

In this example, the width of each shield 220a and 220b (in the Z direction) is preferably selected to shield one detector element 218 at a time although shading of less or more than a whole element is also possible. The length of each shield 220a and 220b (perpendicular to the Z direction) is preferably selected to shield at least one or a plurality of detector elements during a significant fraction of a view time while the gantry rotates. The "view time" duration is defined herein as the time during which the detector array collect one set of projection data. If, for example, the CT scanner is made to acquire 720 views every rotation, detector element "sweep" an angle of 0.5° during each view acquisition. Typically, in a divided detector array 208, the size of a detector element in the X direction is selected to match or to be smaller than the "sweep" an angle during a "view time". Shields 220a that cover 0.2° to 0.5° of the cylinder circumference would shield detector elements for 0.4 to 1 view time, giving good results, although larger or smaller values can be used too. For a system with cylinder 230a diameter of 700 mm, shields 220a and 220b length would typically be in the range of 2.5 mm to 7 mm. For a scanner acquiring 1440 views per rotation, half of said length would be preferable. Note that in this embodiment, detector elements in only some of the detector rows are subject to being shielded. In the example of FIG. 3a detector elements from 5 rows are being shielded at certain angles. In preferred embodiments shields 220a and 220b are staggered in the X direction (perpendicular to Z direction), so detector elements of the same column (parallel to the Z direction) are preferably not shielded at the same time. In some CT scanners the detector array may not be accurately aligned respective the gantry and detector rows may not be parallel to the plane of the X ray source rotation trajectory. Further, in some CT scanners detector elements may not be positioned in rows but be staggered in the Z direction. In these cases same shields may shield detector elements or part thereof in different rows at different gantry rotation angle. In some CT scanners the detector may not be divided to discrete elements or detector elements may be substantially smaller than the area shielded by each shield. Still, in these cases the shield 220 shields a different parts of the detector area at each rotational angle.

According to an exemplary of the embodiment, 0.01% to 10% and preferably 0.5% to 1% of the detector area is shielded by the shield, however higher or lower percentage of shielding may be used.

Figure 3B:
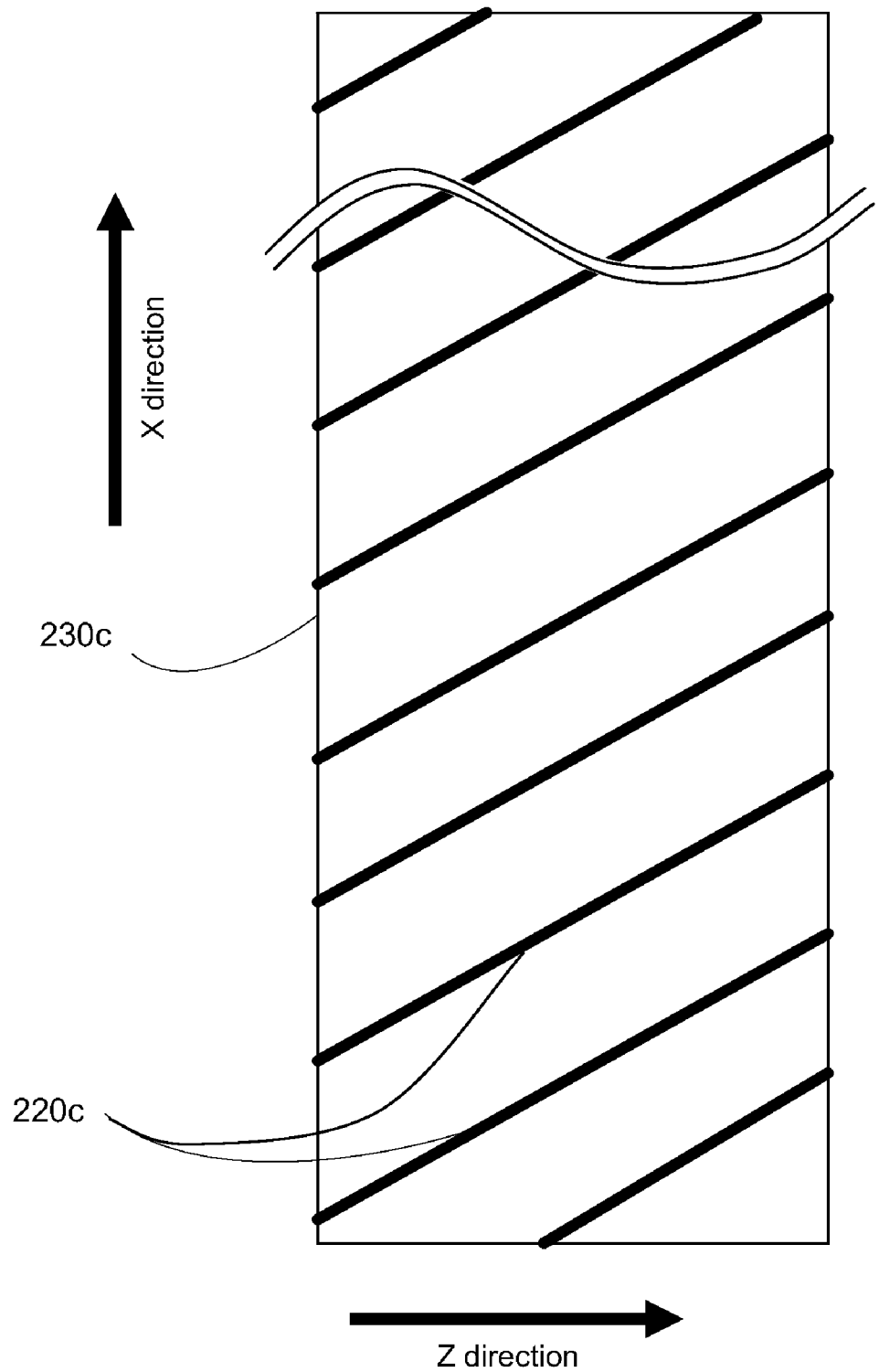
FIG. 3b schematically illustrates a cylinder having a plurality of shields according to another exemplary embodiment of the current invention.

FIG. 3b schematically illustrates another embodiment of the current invention wherein shields 220c are radiation opaque strips or wires disposed on cylinder 230c and operative in a similar manner to shields 220 of FIG. 2 and shield 220a and 220b of FIG. 3a.

Shields 220c shield detector elements in adjacent rows but preferably only limited segments of each column are shielded at a given rotation angle as can be achieved by disposing strip shields 220c diagonal to the Z direction. According to an exemplary of the embodiment, 0.01% to 10% and preferably 0.5% to 1% of the detector area is shielded by the shield, however higher or lower percentage of shielding may be used.

Figure 4A:
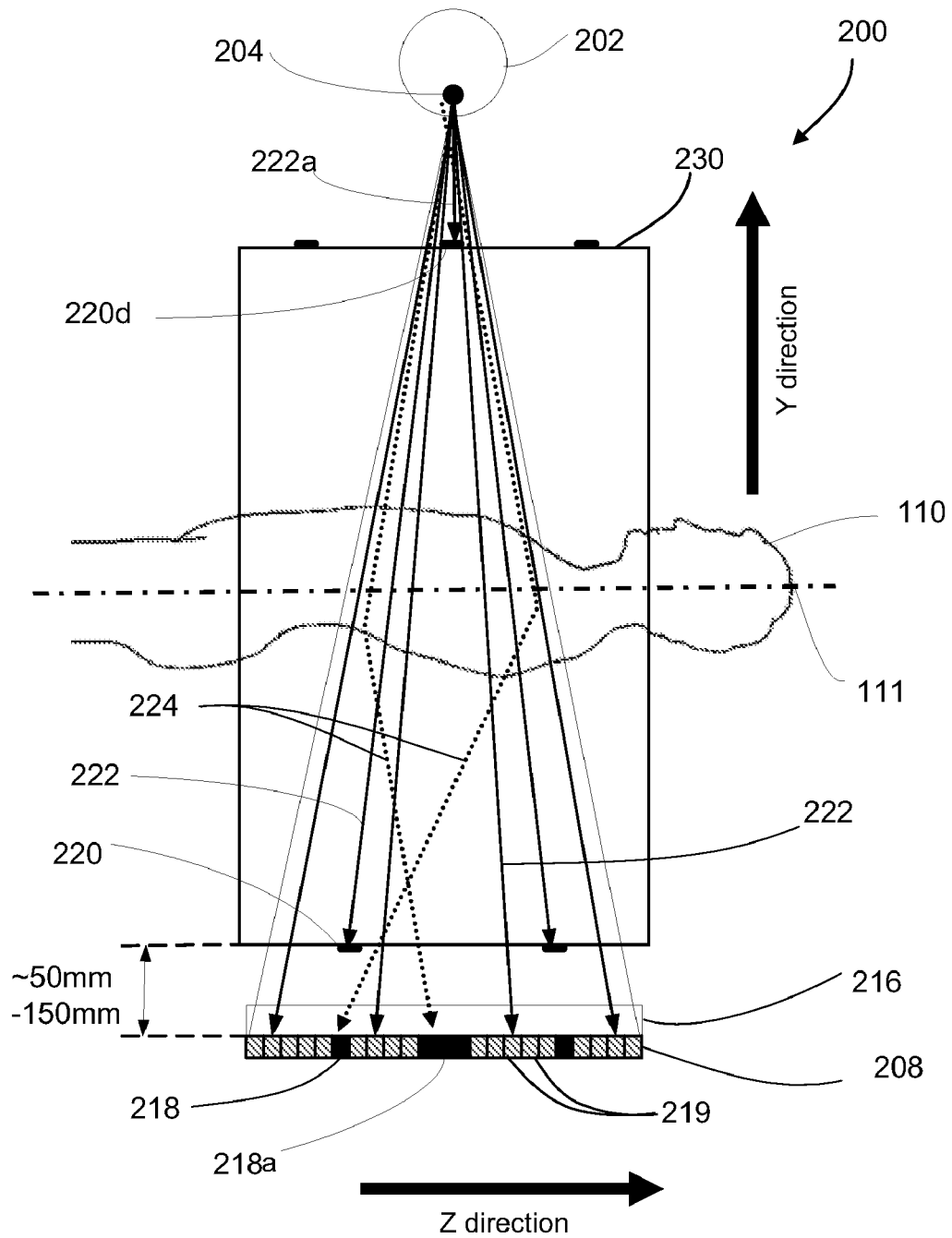
FIG. 4a schematically depicts a side view of a CT system shown in FIG. 2 according to an exemplary embodiment of the current invention.

FIG. 4a schematically depicts a side view of system 200 shown in FIG. 2 according to an exemplary embodiment of the current invention.

In the depicted exemplary embodiment, cylinder 230 may be of the type 230a or 230c depicted in FIG. 3a or 3b respectively comprising shields 220a and 220b or 220c respectively.

In the particular gantry rotation angle shown in FIG. 4a, shield elements 220 are temporarily positioned posterior to the scanned subject 110 and shields detector element or a plurality of elements 218 from direct radiation 222 that has traversed and was attenuated by subject 110. However, at this rotation angle a specific shield element 220d may be temporarily positioned anterior to the subject, in proximity to the radiation source 202 and shields an area 218a of the detector array 208. Shield element 220d may be one of central row shields 220a of FIG. 3a, or the central section of any of shields 220c (seen herein in side cross section) of FIG. 3b. Typically area 218a may include a plurality of detector elements or parts thereof and its boundaries are not well defined due to penumbra effect related to the size of focal spot 204. Shielded areas 218 and 218a are responsive to scattered radiation 224 and not responsive to direct radiation 222. However, the read-out data of shielded detector area 218a is more difficult to correct for the missing direct radiation due to its large extent. Therefore in some preferred embodiments of the invention it is desirable to avoid positioning radiation shields that intercept the beam before it traverses the subject.

Figure 4B:
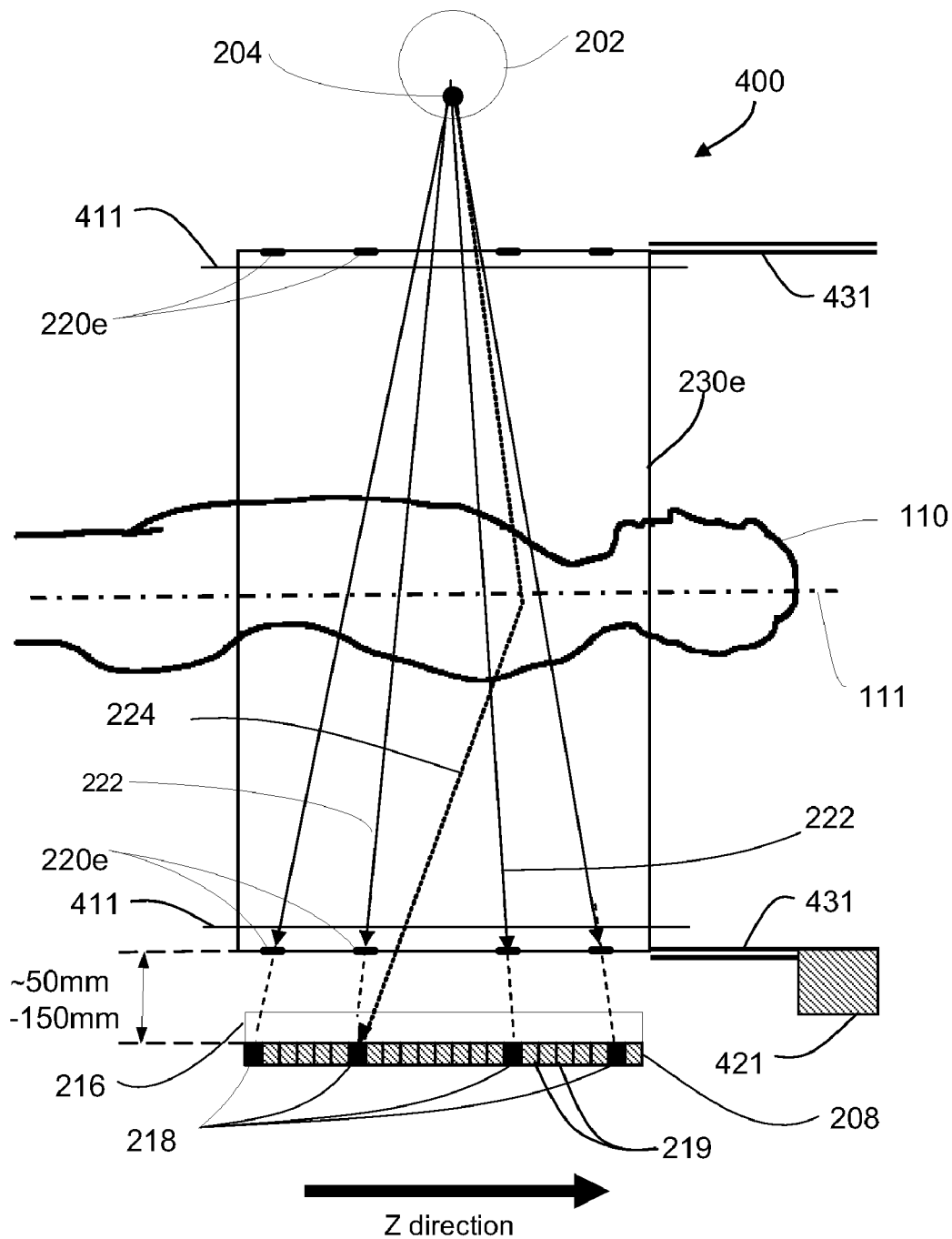
FIG. 4b schematically depicts a side view of a CT system comprising a cylinder with a plurality of shields, wherein the radiation shields are not disposed in the central part of cylinder, according to another exemplary embodiment of the current invention.

FIG. 4b is a side view of system 400 similar to the system 200 shown in FIG. 2 and in FIG. 4a. However, in system 400 radiation shields 220e are not disposed in the center part of cylinder 230e respective the Z axis. Therefore shields 220e are not on the beam path from the X ray focal point 204 towards the subject 110. Yet, because of the divergence of the cone beam, shields 220e intercept the beam path on the detector side of the subject 110.

Figure 5A:
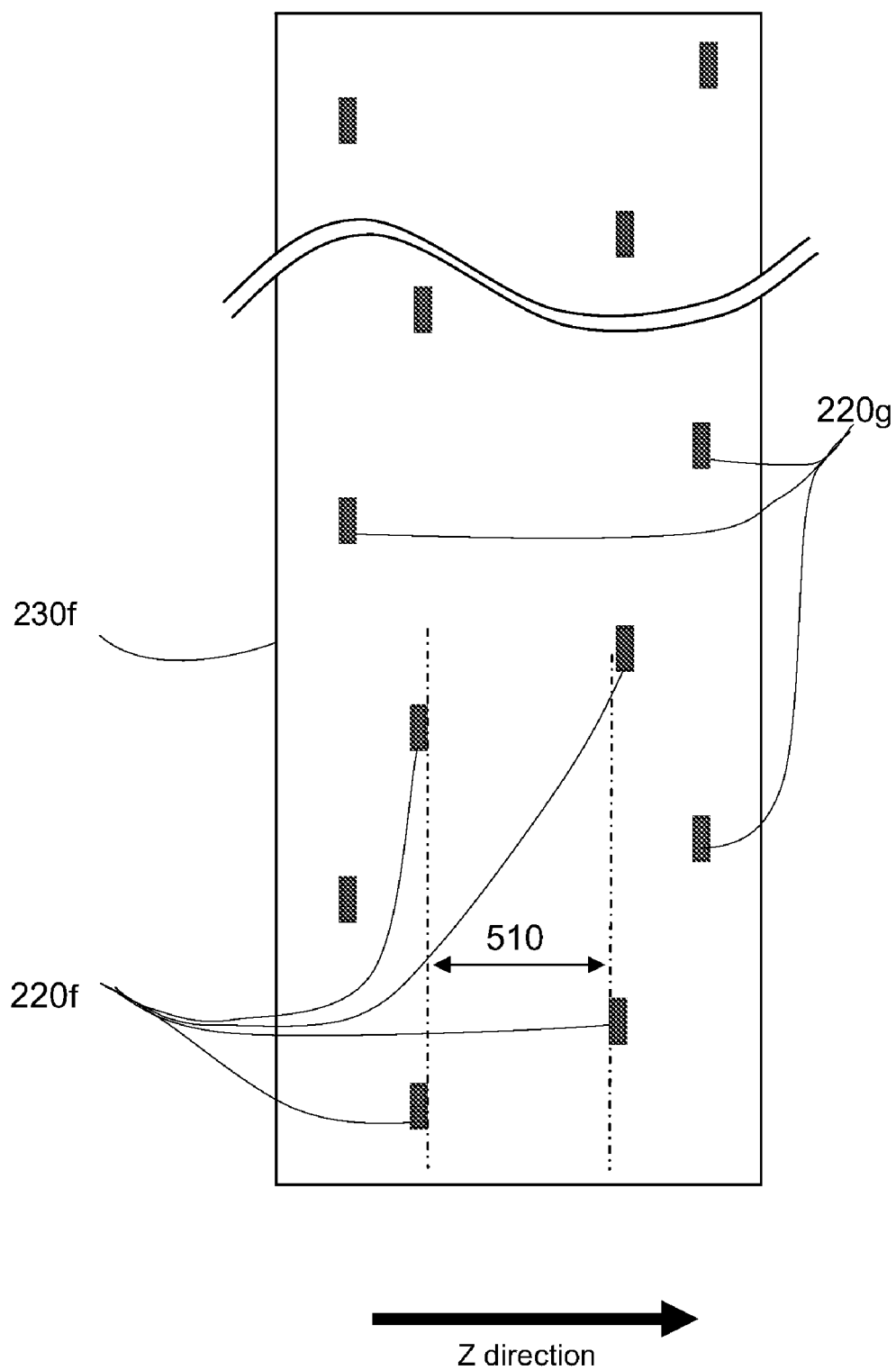
FIG. 5a schematically illustrates a section of the surface of cylinder with a plurality of shields, wherein the radiation shields are not disposed in the central part of cylinder, according to another exemplary embodiment of the current invention.
Figure 5B:
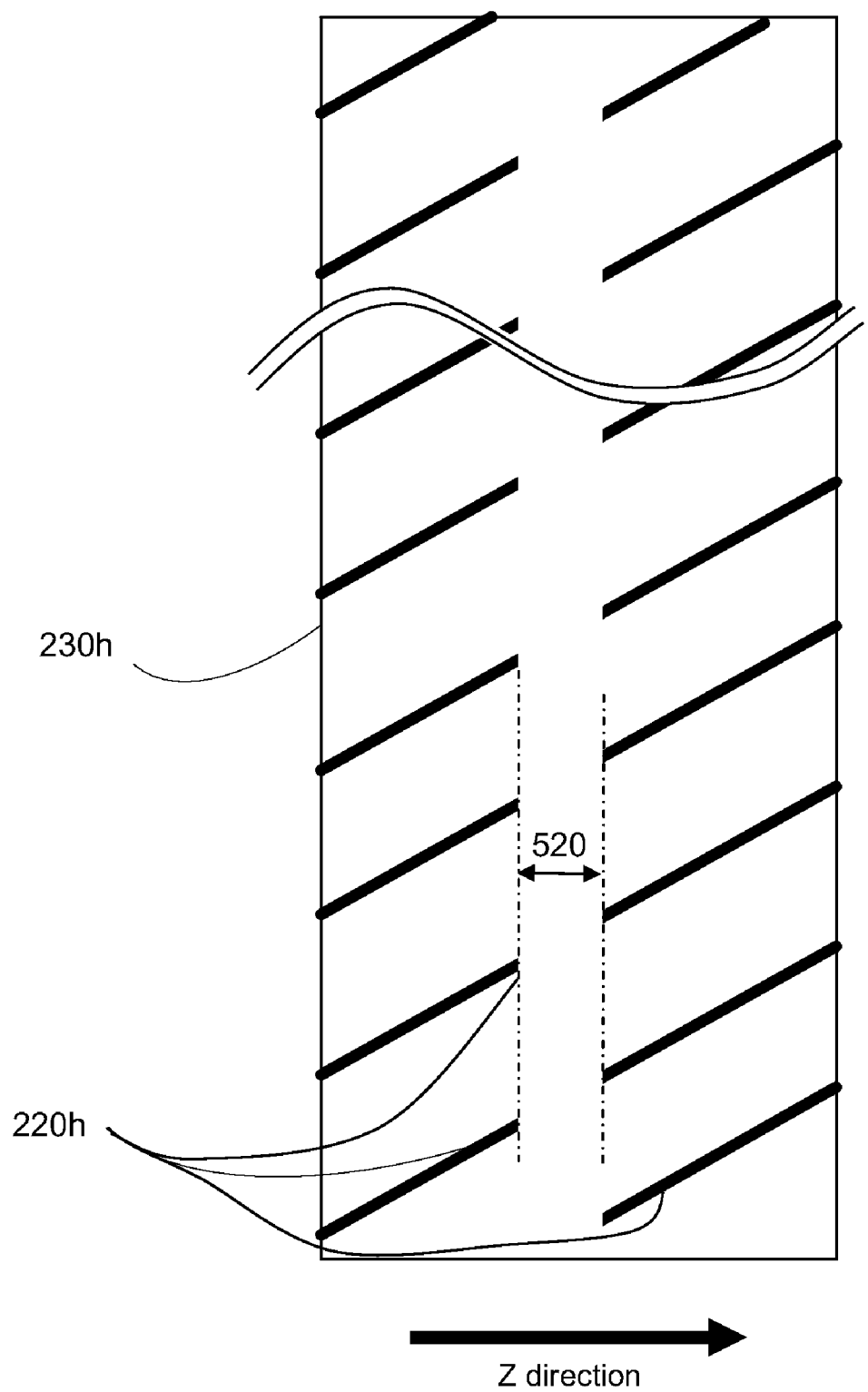
FIG. 5b schematically illustrates a section of the surface of cylinder with a plurality of shields, wherein the radiation shields are not disposed in the central part of cylinder, according to another exemplary embodiment of the current invention.

FIG. 5a and FIG. 5b illustrates exemplary embodiments of the current invention wherein the radiation shields are not disposed in the central part of cylinder 230 respective to Z axis.

FIG. 5a schematically illustrates a section of the surface of cylinder 230f according to an exemplary embodiment of the current invention (the cylinder surface is spread out for the illustration).

In the depicted exemplary embodiments, shields 220f and 220g are arranged in rows aligned with the X direction. However, in contrast to the embodiment depicted in FIG. 3a, the row of shields which is central and substantially aligned with the center of the detector is missing. The spacing 510 between the two central rows of shields 220f is selected such that shields 220f do not intersect with the X ray beam while they are at proximity to the focal point 204. However, different spacing may be used.

Optionally, the rows of shields 220f and 220g (four rows are seen in this exemplary figure, but other number of rows may be used) are symmetrically arranged in respect to the center of the detector. In some embodiments, the distance between rows is identical, however, non-symmetrically arrangement or non-identical distances may be used as well.

According to an exemplary of the embodiment, 0.01% to 10% and preferably 0.5% to 1% of the detector area is shielded by the shield, however higher or lower percentage of shielding may be used.

FIG. 5b schematically illustrates a section of the surface of cylinder 230h according to another exemplary embodiment of the current invention (the cylinder surface is spread out for the illustration). Shields 220h are radiation opaque strips or wires disposed on cylinder 230h and operative in a similar manner to shields 220 of FIG. 2, FIG. 3a and FIG. 4b.

Shields 220h shield detector elements in adjacent rows but preferably only limited segments of each column are shielded at a given rotation angle as can be achieved by disposing strip shields 220h diagonal to the Z direction. However, in contrast to shields 220c of FIG. 3b, a gap having no radio-opaque material is left between shields 220h on the left and the right side in respect to the X axis of cylinder 230h. The spacing 520 between shields 220h is selected such that shields 220h do not intersect with the X ray beam while they are at proximity to the focal point 204. However, different spacing may be used.

Optionally, the shields 220*h* are symmetrically arranged, however other arrangements may be used. According to an exemplary of the embodiment, 0.01% to 10% and preferably 0.5% to 1% of the detector area is shielded by the shield, however higher or lower percentage of shielding may be used.

Returning now to FIG. 4*b*, according to another aspect of the current invention, system 400 further comprises a protective cover 411, separated from cylinder 230*e*. Cover 411 may be a part of the external covers of the CT gantry. According to this embodiment, cylinder 230*e* is configured to slide substantially along the Z direction on optional rails 431 attached to the non-rotating part of the CT gantry (two such rails are seen in this figure, but number of rails may be larger to allow accurate positioning of cylinder 230*e* in respect to the X ray source 202 and detector 208. Optionally, optional actuator 421 such as an electric motor is used for moving cylinder 230*e* along rails 431. However, in some embodiments cylinder 230*e* may be moved manually.

In some embodiments, cylinder 230*e* may slide completely out of the X-ray beam, or to a position wherein none of shields 20*e* intercept the X ray beam. In this configuration, system 400 reverts to the operation of system 100 known in the art.

In some embodiments, wherein cylinder 230*e* is of the type 230*a* of FIG. 3*a*, the cylinder 230*e* may be slightly shifted so that row of shields 220*a* and 220*b* are positioned in front of different rows of detector elements.

Figure 6:
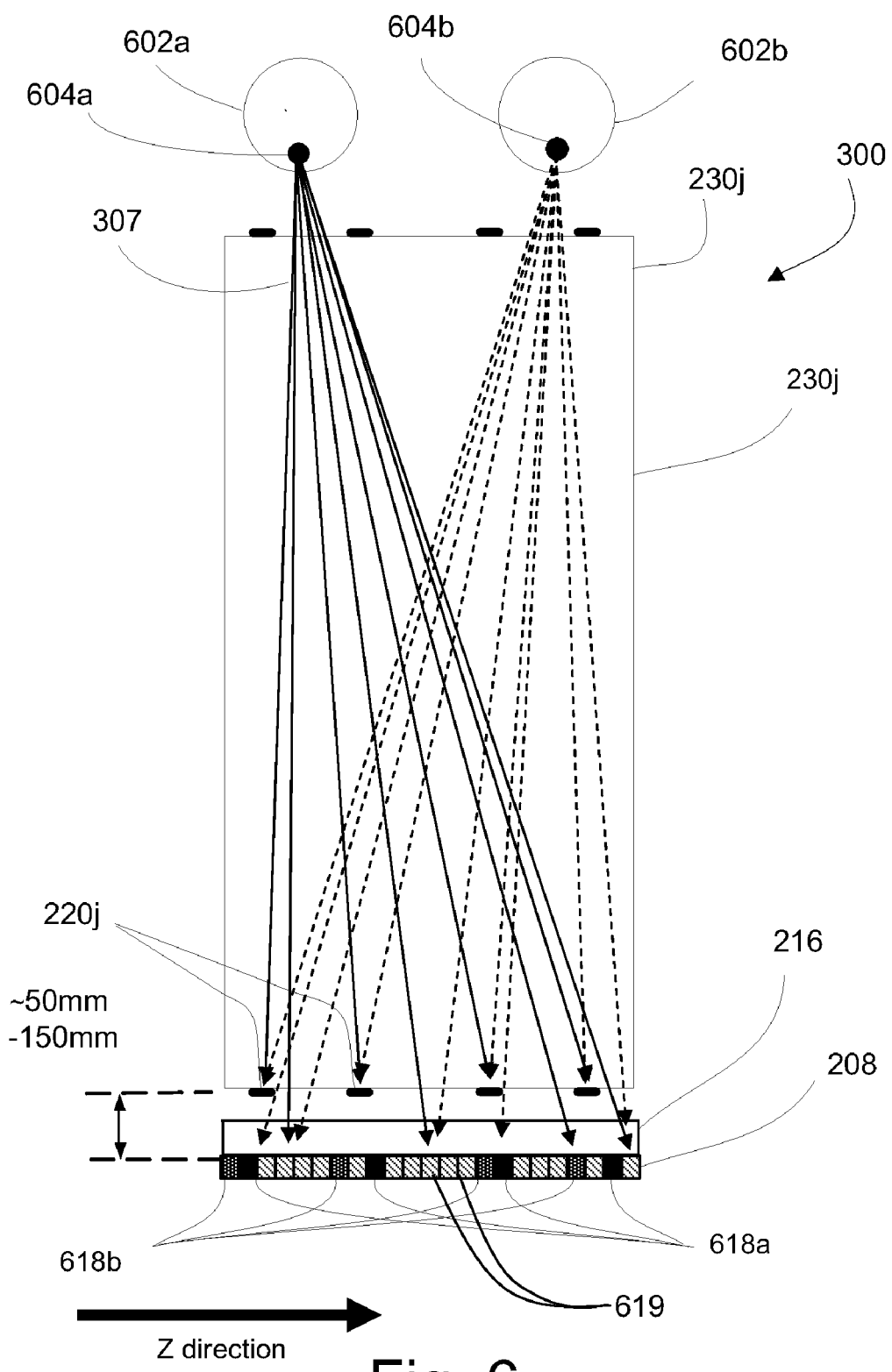
FIG. 6 schematically depicts a CT system having two X ray focal points according to yet another exemplary embodiment of the current invention.

FIG. 6 schematically depicts a CT system 300 having two X ray focal points according to another exemplary embodiment of the current invention.

System 300 is a CT system comprises more than one X-ray source. In the depicted embodiment, system 300 comprising two X ray sources 602*a* and 602*b*, having focal points 604*a* and 604*b* respectively displaced from each other along the Z axis are shown by a way of a non-restrictive example. In other embodiments more than two sources may be provided. The sources may be displaced from each other also in other directions. In this embodiment, the multiple sources irradiate a common detector array 208. Sources 602*a* and 602*b* may be activated alternatively at high switching rate. In some embodiments, focal points 604*a* and 604*b* are multiple focal points of a single X ray tube.

System 300 further comprise a cylinder 230*j* having shields 220*j*. Radiation shields 220*j* are positioned such that at particular gantry rotation angle they block the direct radiation from each X ray source to a set of detector elements, wherein the set of shielded detector elements may be different for each X ray source.

In the depicted example, shields 220*j* shield detector elements 618*a* from direct radiation from focal point 604*a*, while at the same time shields detector elements 618*b* from direct radiation from focal point 604*b*. Preferably, detector elements 618*a* are exposed to direct radiation from focal point 604*b* while detector elements 618*b* are exposed to direct radiation from focal point 604*a*. However, in some embodiments, some detector elements may be shielded from more than one radiation source at specific rotor angle or a plurality of angles. Unshielded detector elements 619 are exposed to direct radiation from both focal points 604*a* and 604*b*. It should be noted that all the detector elements are substantially exposed to scatter radiation from both focal points 604*a* and 604*b* (for clarity, FIG. 6 is drawn without a subject and without scatter radiation).

Preferably, shields 220*j* are situated that they do not block the direct beam while they are in proximity to the X ray source.

In the embodiments described in FIG. 2 to FIG. 6 radiation shields are shown to be disposed on radiation translucent cylinder 230 which is a parts of the CT gantry covers. However, in some embodiments the radiation shields may be disposed on other non-rotating mechanical elements such that they are positioned between the radiation source and the detector. Persons familiar with the art will appreciate that some systems have an open gantry structure (such as a C-arm gantry) and do not have cylinder like member around the scanned subject. In these gantries a special frame may be provided to hold the shields in place. Preferably the shields are positioned at a distance of 50 mm to 150 mm from the detector surface although a smaller or larger distance may be used as well.

Figure 7A:
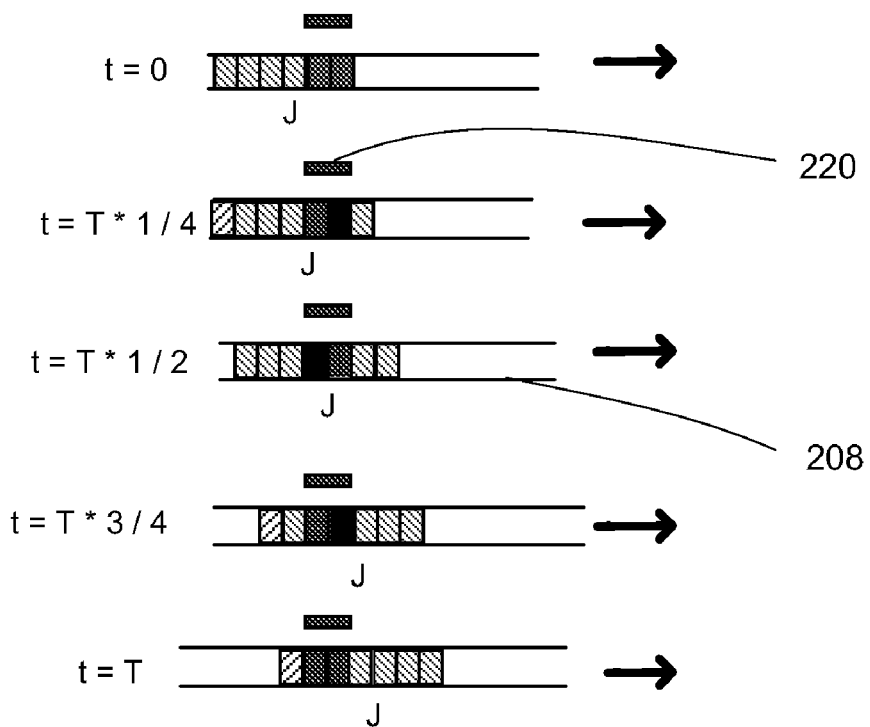
FIG. 7a is a schematic illustration of the shading of detector element J by shield 220 as the detector array is moving relative to the shield due to the rotational motion of the gantry according to an exemplary embodiment of the current invention.

FIG. 7*a* is a schematic illustration of the shading of detector element J by shield 220 as the detector array is moving relative to the shield due to the rotational motion of the gantry according to an exemplary embodiment of the current invention.

The figure shows some elements in a section of detector elements row in detector 208. The system is made to acquire X ray data projections called views during a view time T, wherein, by a way of example, detector elements move four times their width during one view time T. Further, by a way of example the length of the shielding element in the X direction is chosen to cover width of two detector elements. In this example, at t=0, at the start of view time, detector element J just starts being shielded; at t=T/4, detector element J is fully shielded from direct radiation by shield 220; at t=T/2, detector element J is still shielded; starting t=($\frac{3}{4}$)T and on the detector element is again not shielded.

Figure 7B:
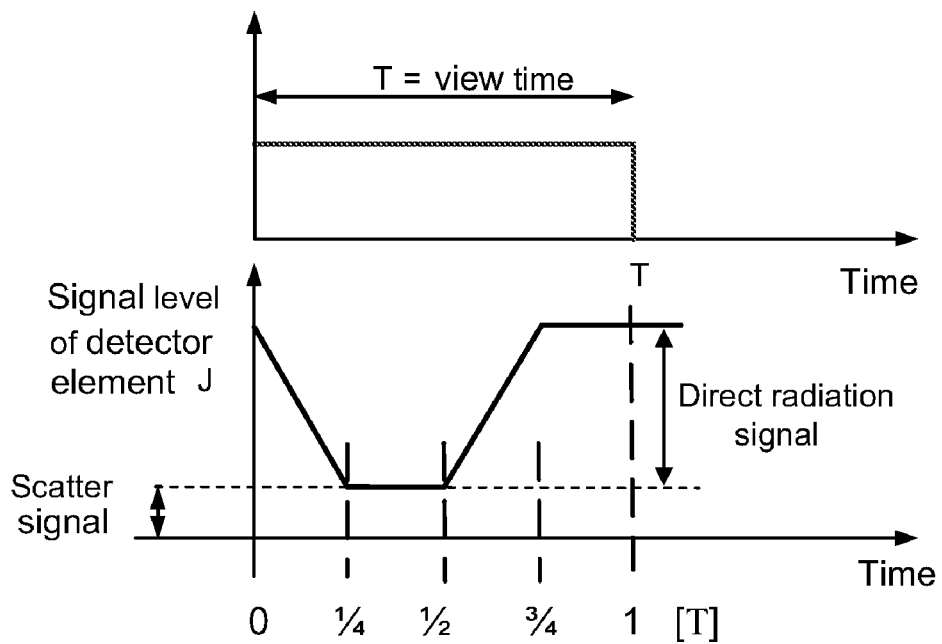
FIG. 7b schematically shows the radiation intensity received by detector element J as a function of time according to an exemplary embodiment of the current invention.

FIG. 7*b* schematically shows the radiation intensity received by the detector element J as a function of time according to an exemplary embodiment of the current invention.

Assuming constant direct and scattered radiation intensity, wherein till t=0 and after t=($\frac{3}{4}$)T the detector element receives both direct and scattered radiation and from T/4 till T/2 the detector element is fully shielded and receives only scattered radiation. In this example, detector element J receives during the view under discussion substantially the full intensity of scattered radiation and ½ of the direct radiation it would have received without the shield. By a way of example, shading was assumed to start just at the start of view time. However, the same relative intensity of direct radiation is received by the shielded detector element J also if shading starts at a later time, up to T/4 in this particular example. Persons skilled in the art will appreciate that other dimensions of shields and detector elements respective to rotation direction and other view sampling rates could be used to provide partial or complete reduction in direct radiation signal for designated detector elements at certain views.

As known in the art, for image reconstruction the readings of the detector elements are corrected for the different gain and offset of each detector element and detector element's readout circuit, as well as possible differences between detector elements in geometrical efficiency and in the un-attenuated (without scanned subject) radiation intensity impinging on the elements. This is typically done by operating the scanner to acquire data without a scanned subject or with known homogeneous absorber, storing the calibration data and using it for normalizing the data acquired with a scanned subject. The procedure is referred at as "air calibration" or as "flat field calibration". In embodiments of the present invention, some detector element readouts are reduced at certain rotation angles due to the shields. According to some exemplary embodiments of the invention, during air calibration, the reduced data are replaced by values interpolated from data acquired for same detector elements at adjacent rotation angles wherein said detector elements are not shielded. Alternatively, in some embodiments the array of shields is removed from the beam path during air calibration and inserted to the beam path during subject scan as described in reference to FIG. 4b. Further, alternatively, in some embodiments with a multiple source CT scanner as described e.g. in reference to FIG. 6, direct data emitted from one focal spot may be used to calibrate detector elements at gantry rotation angles wherein said detector elements are shielded from direct radiation emitted by a second source.

Considering now a projection data (set of data acquired for the detector array during one view) wherein the direct radiation signal for designated detector elements is reduced by a fraction f, wherein f has a value larger than 0 and smaller than 1. Shielded detector elements in particular projection angles and the respective reduction fraction f may be known in advance from the design and operation parameters of the system or may be determined by prior calibration using methods well known in the art. For example, f values may be determined by a prior calibration scan without a scattering subject and comparison of the measured signals for shielded detectors with the signals measured for same detectors before and after they are shielded. In embodiments where the shields array is movable as shown e.g. in FIG. 4b, f values may be determined by measuring signal intensity with and without the shields.

In preferred embodiments f is designed to be about 0.5 (for views of highest shading) although higher or lower values may be used as well. For simplicity it is assumed in the discussion below the same value of f is applied to all shielded detectors elements although different values of f can be used for different shielded elements and different views.

Let $R(i,j)$ be the air calibration corrected raw data received by detector element at row i and column j in a subject scan, We denote $R(i,j)=D(i,j)+S(i,j)$ wherein $D(i,j)$ corresponds to direct radiation from the X ray source (that was attenuated by the subject) and $S(i,j)$ corresponds to scattered radiation, Let $(k,l)$ be a subset of $(i,j)$ corresponding to detector elements which are shielded by shields in a particular view. The subset $(k,l)$ is different for each projection of the scan, wherein for some shields design as shown e.g. in FIG. 3a and 5a there may not be shielded elements at all for some of the projections and for other shields design as shown e.g. in FIG. 3b and 5b there are shielded elements in every projection.

In these embodiments the air calibration is corrected for the effect of the shields as described hereinabove. Therefore, normalization of the measured data by the air calibration data yields:

$$R(k,l)=fD(k,l)+S(k,l)$$

For example, for $$f=0.5: R(k,l)=0.5D(k,l)+S(k,l)$$

The data may optionally be processed in the following way to extract the scattered radiation and correct for it:
i) The shielding fractions f are determined for the (k,l) array as described hereinabove ahead of the scan.
ii) For each view the subset (k,l) of shielded detector elements is determined based on prior knowledge of the system's geometry, prior calibration or identification of channels with low readout compared to neighbors. Elements shielded for less time or area than designated are excluded;
iii) The values of $D(k,l)+S(k,l)$ that would have been obtained without the shields for the shielded detector elements are determined by interpolation of the measured values $R(i,j)$ of un-shielded neighbors;
iv) The values of direct radiation $D(k,l)$ for the shielded detector elements are determined by subtraction of the measured results $R(k,l)$ from the interpolated results $D(k,l)+S(k,l)$ and normalization by $1/(1-f)$;
v) The values of scattered radiation $S(k,l)$ for the shielded detector elements are determined by subtraction of the calculated direct radiation $D(k,l)$ from the interpolated $D(k,l)+S(k,l)$ results;
vi) The values of the scatter radiation $S(i,j)$ for the un-shielded detector elements are determined by interpolation, as described hereinbelow, of the scattering $S(k,l)$ of the shielded elements so achieved, to fit of a scatter map for the rest of the detector area;
vii) The values of the scattered radiation $S(i,j)$ in preceding or subsequent views wherein there are no shielded detector elements are determined by interpolation of the scatter map across the range of rotation angles;
viii) The direct radiation $D(i,j)$ for the un-shielded detector elements is determined by subtraction of the interpolated scattered data $S(i,j)$ from the measured raw data $R(i,j)$;
ix) The direct radiation $D(k,l)$ for the shielded or partially shielded detector elements may be re-determined by interpolation from the $D(i,j)$ values of un-shielded neighbors and/or from the $D(i,j)$ values acquired for same detector elements before and after they were shielded.

Considering the specific case wherein designated detector elements are completely or nearly completely shielded from direct radiation at certain views, $S(k,l)=R(k,l)$ is the scattered radiation at shielded detector element $(k,l)$. The same procedure as described is optionally applied except that steps iii-v are not needed.

As known in the art, the intensity of the scattered radiation $S(i,j)$ is a slow varying function along the rows and columns of the array, as compared to the fast variation observed frequently for the direct radiation function $D(i,j)$. Therefore, the scattered radiation of the un-shielded detector elements may optionally be determined by interpolation of the data $S(k,l)$ determined for sub-set $(k,l)$ to the entire set $S(i,j)$. The interpolation in this step and in other steps and embodiments hereinbelow may be linear or preferably quadratic spline or higher order spline interpolation or by any other interpolation algorithm known in the art. Alternatively, a scatter map $S(i,j)$ may optionally be generated for the detector array by a fit of a smooth function such as polynomial function to the $S(k,l)$ data by methods known in the art.

Embodiments of the present invention are provided with a controller adopted to carry out the scatter subtraction from the raw data using algorithms as described hereinabove. Persons experienced in the art will appreciate there are other algorithms to deduce the values of the direct and scattered radiation and subtract the scattered radiation. These algorithms are also covered by the invention in as much they use the data measured for the shielded and un-shielded detector elements to correct the data for the entire array.

In some embodiments scatter correction based solely on measurement of scattered radiation by shielded detector elements and computation of the scattered versus direct components of the radiation received by a detector array as described hereinabove. In other embodiments scatter correction is based on measurements by shielded detector elements combined with other scatter calibration methods and correction algorithms known in the art.

Preferred embodiments are described by a way of a non restrictive example as using detector arrays with discrete detector elements. However, the invention applies also to detector arrays without discrete elements, wherein a limited area of the array may be shielded at a time, or to detector arrays with small elements (e.g. below 1 mm) wherein groups of detector elements may be fully or partially shielded by shields, or to single slice CT scanners with one row of detector elements.

Further, preferred embodiments are described by a way of a non restrictive example as comprising a cylinder shaped frame carrying the shielding elements. However other shaped frames may be applicable as well.

Further, preferred embodiments are described by a way of a non restrictive example as using a rotating gantry which carries the X ray source or sources and detector array (known in the art as third generation CT). However, the invention applies also to CT wherein the detector array is static (known in the art as fourth generation CT), the X ray source is made to move by electronic rather than mechanical means (known in the art as electron beam CT), CT scanners comprising multiple sources arranged circumferentially to the scanned subject which are operative to irradiate said subject from multiple directions and cone beam CT with circular or non-circular focal spot trajectories.

Further, preferred embodiments are described by a way of a non restrictive example as applicable to medical imaging. However, the invention applies also to non medical imaging of non-human subjects such as non-destructive testing and homeland security imaging.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed:

1. A method for CT imaging of a subject while correcting for scattered radiation, the method comprising:
   a. providing a CT scanner comprising at least a first source of X ray radiation capable of rotating about the subject and a detector capable of receiving radiation that has been attenuated by the subject;
   b. providing an array of radiation shields, said shields being operative to shield parts of an area of the detector from the X ray source at some source rotation angles and not to shield same parts of the detector area at other source rotation angles of said X ray source;
   c. irradiating said subject by said first X ray source while the source is rotating about said subject and acquiring X ray data from said detector, wherein X rays received by said detector comprise direct radiation from the source that was attenuated by said subject and scattered radiation that was scattered by said subject, and wherein parts of the detector area are substantially irresponsive to direct radiation and responsive to scattered radiation while they are shielded from said first X ray source by said shields;
   d. computing scattered radiation data indicative of the part of the X-ray data due to scattered radiation for all parts of the detector area at all rotation angles, said computation being based on data received by parts of the detector area while shaded by said shields; and
   e. correcting the data acquired by parts of the detector area not shielded by said shields by substantially subtracting said computed scattered radiation data from the total measured data.

2. The method according to claim 1 and further comprising correcting data received by parts of the detector while shaded by the shields, wherein said correction is based on data received by parts of the detector while not shaded by said shields.

3. The method according to claim 1 and further comprising reconstructing at least one image based on said corrected data.

4. The method according to claim 1 wherein said first X ray source and said detector are mounted on a rotating frame and said array of shields is mounted on a non rotating frame.

5. The method according to claim 1, wherein said detector is divided into detector elements and said shields comprise radiation opaque material substantially blocking direct radiation from reaching a part of an active area of shielded detector elements at certain source rotation angles.

6. The method according to claim 1, wherein said array of radiation shields is disposed on a cylinder made of radiation translucent material situated around said subject.

7. The method according to claim 6, wherein said array of shields comprises strips of radiation opaque material disposed on said cylinder.

8. The method according to claim 1, wherein said shields are positioned out of the beam path when said shields are proximate to said source and are positioned in the beam path when said shields are far from the source, as the source rotates about the subject.

9. The method according to claim 1, wherein the CT scanner further comprises a second X ray source displaced from said first X ray source.

10. The method according to claim 9, wherein multiple sources are operable to irradiate a common detector area, wherein said shields are configured to shield direct radiation from said first X ray source from reaching certain parts of the detector at certain rotation angles, said certain parts capable to receive direct radiation from said second X ray source at the same rotation angle.

11. The method according to claim 1, wherein the process of the scatter correction comprises a fit of a scatter map for an area of the detector, based on the readout of said shielded detector elements.

12. The method according to claim 11, wherein said fit comprises using a polynomial function.

13. The method according to claim 1, wherein the process of the scatter correction comprises performing spatial interpolation on read out of shielded detector elements.

14. The method according to claim 13, wherein said spatial interpolation comprises cubic or higher order spline interpolation.

15. The method according to claim 1, wherein said shields are movable out of the beam path or to a different position in the beam path.

16. A system for CT imaging of a subject while correcting for scattered radiation, the system comprising:

a. at least a first source of X ray radiation capable of rotating about the subject;
b. a detector capable of receiving radiation that has been attenuated by said subject;
c. an array of radiation shields, said shields being operative to shield parts of an area of said detector from said first X ray source at some source rotation angles and not to shield same parts of an area of the detector at other source rotation angles;
d. a controller capable of irradiating said subject by the X ray source while the source is rotating about the subject and acquiring X ray data from said detector, wherein X rays received by said detector comprise direct radiation from the source that was attenuated by the subject and scattered radiation that was scattered by the subject, and wherein parts of the detector area are substantially irresponsive to direct radiation and responsive to scattered radiation while they are shielded from the X ray source by said shields;
e. a first image processor capable of computing the part of the X-ray data due to scattered radiation for all parts of the detector area at all rotation angles, said computation being based on data received by parts of said detector area while shielded by said shields; and
f. a second image processor capable of correcting the data received by parts of the detector area not shielded by the shields by subtraction of the computed scattered radiation data from the total measured data.

17. The system according to claim 16 and further comprising a third image processor capable of correcting the data received by parts of the detector shielded by said shields, wherein said correction is based on data received by parts of the detector not shielded by said shields.

18. The system according to claim 17, and further comprising a fourth image processor capable of reconstructing images of said subject.

19. The system according to claim 16 wherein said X ray source and said detector are mounted on a rotating frame and the array of shields is mounted on a non rotating frame.

20. The system according to claim 16, wherein said detector is divided into detector elements and said shields comprise radiation opaque material that block substantially all direct radiation from reaching shielded detector elements at certain source rotation angles.

21. The system according to claim 16, and further comprising a cylinder made of radiation translucent material situated around said subject and said shields comprise of elements of radiation opaque material disposed on said cylinder.

22. The system according to claim 21, wherein said shields comprise strips of radiation opaque material disposed on said cylinder.

23. The system according to claim 16, wherein said shields are positioned out of the beam path when said shields are proximate to said first X ray source and are positioned in the beam path when said shields are far from said X ray source, as the source rotates about the subject.

24. The system according to claim 16, and further comprising at least a second X ray sources displaced from said first X ray source.

25. The system according to claim 24, wherein multiple sources are operable to irradiate a common detector area, wherein said shields are operable to shield direct radiation from said first X ray source from reaching certain parts of the detector at certain rotation angles, said certain parts capable to receive direct radiation from said second X ray source at the same rotation angle.

26. The system according to claim 16, wherein said process of the scatter correction comprises a fit of a scatter map for an area of said detector, based on the readout of shielded detector elements.

27. The system according to claim 26, wherein said fit comprises using a polynomial function.

28. The system according to claim 16, wherein said process of the scatter correction comprises performing spatial interpolation on readout of shielded detector elements.

29. The system according to claim 28, wherein said spatial interpolation comprises cubic or higher order spline interpolation.

* * * * *